US00PP21049P2

(12) United States Plant Patent
Giesen

(10) Patent No.: US PP21,049 P2
(45) Date of Patent: Jun. 1, 2010

(54) ***LOBELIA* PLANT NAMED 'TECH HEPDAB'**

(50) Latin Name: *Lobelia erinus*
Varietal Denomination: Tech Hepdab

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 91 days.

(21) Appl. No.: 12/288,665

(22) Filed: Oct. 22, 2008

(51) Int. Cl.
*A01H 5/00* (2006.01)

(52) U.S. Cl. ..... Plt./451

(58) Field of Classification Search ..... Plt./451
See application file for complete search history.

(56) References Cited

U.S. PATENT DOCUMENTS

PP16,112 P3 * 11/2005 Oud ..... Plt./451
PP17,250 P2 * 11/2006 Giesen ..... Plt./451

OTHER PUBLICATIONS

UPOV ROM GTITM Computer Database, GTI Jouve Retrieval Software 2009/05 Citation for 'Tech Hepdab'.*

* cited by examiner

*Primary Examiner*—Wendy C. Haas
(74) *Attorney, Agent, or Firm*—S. Matthew Edwards

(57) ABSTRACT

A new *Lobelia* plant named 'Tech Hepdab,' particularly distinguished by deep blue flowers with distinct white eyes, deep green foliage, initially upright stems, semi-upright, medium vigor, and about medium sized, mounding plant habit with long inflorescences above the foliage, and relatively good heat tolerance.

1 Drawing Sheet

Latin name of the genus and species of the plant claimed: *Lobelia erinus.*

Varietal denomination: 'Tech Hepdab'.

BACKGROUND OF THE NEW PLANT

The present invention comprises a new and distinct cultivar of *Lobelia*, botanically known as *Lobelia erinus* and hereinafter referred to by the cultivar name 'Tech Hepdab'.

'Tech Hepdab' is a product of a planned breeding program. The new cultivar originated from a hybridization made in June 2005 in Andijk, Netherlands.

The female parent was an unpatented proprietary *Lobelia* plant designated 'LOB04-315-2' with dark blue flowers. 'LOB04-315-2' has larger leaves and has a less upright plant habit than 'Tech Hepdab'.

The male parent of 'Tech Hepdab' was an unpatented proprietary *Lobelia* plant designated 'LOB04-307-4' having blue flowers with white eyes. 'LOB04-307-4' has a larger plant habit with longer stems than 'Tech Hepdab'.

The resulting seeds were sown in October 2005. 'Tech Hepdab' was selected as one flowering plant within the progeny of the stated cross in January 2006 in a controlled environment in Andijk, Netherlands.

The first act of asexual reproduction of 'Tech Hepdab' was accomplished when vegetative cuttings were taken from the initial selection in the spring of 2006 in a controlled environment in Andijk, Netherlands.

Horticultural examination of plants grown from cuttings of the plant initiated in the spring of 2007 in Andijk, Netherlands, and in Hillscheid, Germany, and continuing thereafter, has demonstrated that the combination of characteristics as herein disclosed for 'Tech Hepdab' are firmly fixed and are retained through successive generations of asexual reproduction.

'Tech Hepdab' has not been observed under all possible environmental conditions. The phenotype may vary significantly with variations in environment such as temperature, light intensity and day length.

A Plant Breeders' Right for this cultivar was applied for with the European Union on Jul. 21, 2008. 'Tech Hepdab' has not been made publicly available more than one year prior to the filing of this application.

DESCRIPTION OF THE DRAWINGS

This new *Lobelia* plant is illustrated by the accompanying photograph which shows blooms, buds, and foliage of the plant in full color. The colors shown are as true as can be reasonably obtained by conventional photographic procedures. The photograph, taken in late May 2008, is of three 13–14 week old plants grown in a 25 cm diameter pot/bowl in a greenhouse during a spring trial setting. The inset shows a close view of a single flower.

DETAILED BOTANICAL DESCRIPTION

The measurements were taken in Hillscheid, Germany, on Aug. 30, 2008 on 22 week old plants that were growing in 25 cm diameter bowls indoors and hanging baskets outdoors under rain protection. Culture of these plants had started in late March 2008 with planting of rooted cuttings into 12 cm pots. The young plants were pinched once. Cultivation was on benches in a greenhouse at relatively cool temperatures.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Lobelia* as a new and distinct variety:

1. Relatively large, dark blue flowers with a distinct white eye.
2. Deep green foliage, lanceolate leaves.
3. Well branched, moderately tight, mounding plant habit.
4. Medium vigor and about medium in size.
5. Relatively good heat tolerance (for a *Lobelia*) due to the partly pubescent stem and leaf surfaces.

COMPARISON WITH COMMERCIAL CULTIVARS

'Tech Hepdab' differs from the commercial cultivar 'Laguna Compact Blue With Eye' ('Lobetis,' U.S. Plant Pat. No. 16,112) in that 'Tech Hepdab' has darker blue flowers, deeper green foliage and more upright habit than 'Lobetis'.

'Tech Hepdab' differs from the commercial cultivar 'Techno Blue' ('Lob Bule,' U.S. Plant Pat. No. 17,250) in that 'Tech Hepdab' has darker blue flowers with a more distinct eye and more upright plant habit than 'Lob Bule'.

'Tech Hepdab' differs from 'Tech Darbule' (U.S. plant application Ser. No. 12/284,571) by somewhat larger flowers, even deeper blue overall flower color and different markings on petals: 'Tech Hepdab' has two relatively large white 'eyes,' while 'Tech Darbule' has two small white macules and 3 dark blue dots. Additionally, 'Tech Hepdab' develops somewhat stronger anthocyanin coloration of the sepals, and has a generally more upright plant habit than 'Tech Darbule'.

Plant:

*Growth and habit.*—Medium vigor, bushy plant habit with initially upright directed stems, later semi-upright and mounding, Moderately tight.

*Form.*—Mounding, semi-spherical shape.

*Height.*—21–22 cm (from top of soil) for 22 week old plants.

*Width* (*diameter*).—40–45 cm.

*Plant spread* (*including flowers*).—Approximately 30–35 cm, from the base of the main stem to the tips of the branches.

*Number of branches.*—Roughly 70–80.

*Time to produce a finished flowering plant.*—About 12 weeks for a 12 cm pot.

*Outdoor plant performance.*—Used in patio containers, in hanging baskets or in mixed container plantings mainly.

*Time to initiate and develop roots.*—Approximately 24 days at 20–24° C.

*Root description.*—Fibrous and freely branching.

Stem:

*Characteristics.*—Cross section square with slightly strengthened corners, side branches emerging mainly from the lower nodes of the stem.

*Stem length.*—25–32 cm.

*Diameter.*—2–3 mm.

*Internode length.*—1.0–2.5 cm.

*Color.*—RHS 137A.

*Texture.*—Covered with pubescence.

Foliage:

*Arrangement.*—Alternate.

*Shape.*—Broadly ovate to elliptical, oblanceolate, on flowering stems usually narrow lanceolate, sessile, no distinct petiole.

*Apex.*—Acute.

*Base.*—Attenuate to cuneate.

*Margin.*—Crenate.

*Leaf length* (*in flowering stage*).—Up to 5.0 cm.

*Leaf width.*—Up to 1.5 cm.

*Color upper surface.*—RHS 137A or RHS 139A, young leaves at the shoot tips can be both lighter in color, or deep green with a shade of anthocyanin (purple).

*Color lower surface.*—RHS 138A.

*Venation type.*—Pinnate.

*Venation color.*—Upper surface: Indistinct, same as the leaf blade. Lower surface: RHS 144A.

*Texture.*—Both surfaces covered with short hair, sparse on the upper surface.

Inflorescence:

*Blooming habit.*—Continuous through the growing season from spring to the fall.

*Start of flowering.*—About 10 weeks after planting of rooted cuttings in spring

*Lastingness of individual blooms on the plant.*—5–7 days, depending on temperature mainly.

*Fragrance.*—None.

*Type of inflorescence.*—Terminal raceme.

*Quantity of flowers per stem.*—Most often 3 to 5 open flowers, and additional buds.

*Length of inflorescence.*—14–17 cm.

*Length of peduncle.*—12–15 cm.

*Diameter of peduncle.*—2.5 mm.

*Color of peduncle.*—Deep green, RHS 137A.

*Texture of peduncle.*—Rough with short hair, hirtellous.

Flower:

*Corolla type and shape.*—Single, zygomorphic; lower part tube to funnel shaped, with the petal lobes opening outwards; and 2 small petals upright directed and 3 mainly fused petals forming the lower lip.

*Corolla flower diameter, length.*—1.9–2.1 cm.

*Flower width.*—2.0–2.2 cm.

*Tube/funnel length.*—0.9 cm.

*Tube diameter.*—0.4 cm.

*Color upper surface.*—RHS 95A to 95B, deep blue.

*Color lower surface.*—Somewhat variable, from RHS 96D to 97A and 97B, color fading towards base.

*Markings in the center.*—Relatively large white 'eye,' RHS 155D, and 2 yellow green 'spots' N144A.

Petal (lobes):

*Apex.*—Mucronulate.

*Base.*—Fused, forming a tube or narrow funnel.

*Margin.*—Entire.

*Texture.*—Both surfaces mainly glabrous, short hair along the edges and the veins in the eye zone.

*Lower lip, length.*—1.0–1.2 cm.

*Lower lip, width.*—1.8–2.0 cm.

*Upper lobes, length* (*from the corolla opening*).—0.7–0.8 cm.

*Upper lobes, width.*—2.3 mm.

*Lower lobes, length* (*from the corolla opening*).—Up to 1.2 cm.

*Lower lobes, width.*—0.7–0.8 cm.

Flower bud:

*Shape.*—Elongate.

*Diameter.*—0.4–0.5 cm.

*Length.*—1.2–1.4 cm.

*Color* (*at tight bud*).—RHS 95C to mainly 97A, light blue.

Calyx:

*Form and shape.*—5 sepals, fused at the base, slanting upwards.

*Sepal color.*—RHS 139A, dark green with a trace of anthocyanin, for both surfaces.

*Length.*—0.7–0.8 cm.

*Width.*—0.1–0.2 mm.

*Shape of sepal.*—Ligulate.

*Apex.*—Acute, pointed.

*Base.*—Fused.

*Texture.*—Densely covered by short hair, both surfaces.

Pedicles:

*Color.*—RHS 137C, green.

*Length.*—2.0–2.5 cm.

*Diameter.*—0.1 cm.

*Texture.*—Covered by short hair.

Reproductive organs:

Stamens:

*Quantity.*—5, coherent.

*Filament, color.*—RHS 96A to 96D, fading towards base

*Filament length.*—0.7–0.8 cm.

*Diameter.*—0.1 cm.

*Anther color.*—Approximately RHS N200A.

*Pollen amount.*—Sparse.

*Pollen color.*—RHS 8B.

Pistil:

*Quantity per flower.*—One, capitate.

*Length.*—1.3 cm.

*Stigma color.*—Near RHS N79D, dull purple.

*Style color.*—RHS 145A.

Fruit and seed set: Has not been observed.

Disease/pest resistance: Disease resistance or susceptibility other than typical for the species has not been observed on this hybrid.

What is claimed is:

1. A new and distinct variety of *Lobelia* plant named 'Tech Hepdab,' substantially as illustrated and described herein.

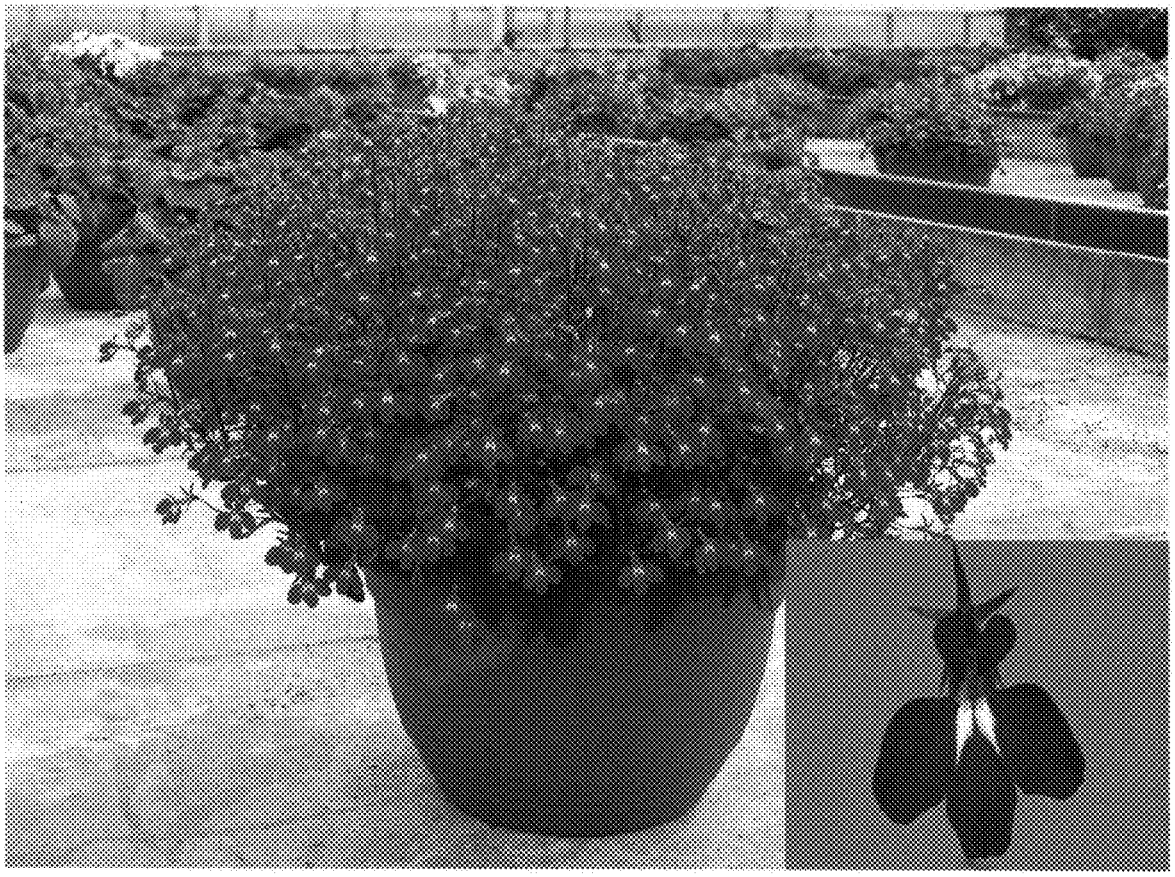

* * * * *